US00PP25696P3

(12) United States Plant Patent
Clark et al.

(10) Patent No.: US PP25,696 P3
(45) Date of Patent: Jul. 14, 2015

(54) GRAPE PLANT NAMED 'FAITH'

(50) Latin Name: ***Vitis labrusca* L.×*Vitis vinifera* L.**
Varietal Denomination: Faith

(71) Applicant: THE BOARD OF TRUSTEES OF THE UNIVERSITY OF ARKANSAS, Little Rock, AR (US)

(72) Inventors: John Reuben Clark, Fayetteville, AR (US); James N. Moore, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 181 days.

(21) Appl. No.: 13/987,501

(22) Filed: Jul. 31, 2013

(65) Prior Publication Data

US 2015/0040279 P1 Feb. 5, 2015

(51) Int. Cl.
*A01H 5/00* (2006.01)

(52) U.S. Cl.
USPC ..... Plt./206

(58) Field of Classification Search
USPC ..... Plt./206
See application file for complete search history.

(56) References Cited

U.S. PATENT DOCUMENTS

PP13,309 P2 12/2002 Clark et al.
2012/0297511 P1 11/2012 Clark et al.

OTHER PUBLICATIONS

U.S. Appl. No. 13/987,494, filed Jul. 31, 2013.
U.S. Appl. No. 13/987,496, filed Jul. 31, 2013.
U.S. Appl. No. 13/987,497, filed Jul. 31, 2013.

*Primary Examiner* — Annette Para
(74) *Attorney, Agent, or Firm* — Andrus Intellectual Property Law, LLP

(57) ABSTRACT

Description and specifications of a new and distinct grapevine cultivar named 'Faith' which originated from a hand-pollinated cross of A-1962 (non-patented, non-released breeding genotype)×Jupiter (U.S. Plant Pat. No. 13,309) made in 1990. This new grapevine cultivar can be distinguished by its seedless, blue/black berries of with neutral and occasional slight fruity flavor, medium sized clusters, medium vigor, and healthy plant.

3 Drawing Sheets

Latin name: *Vitis labrusca* L.×*Vitis vinifera* L.
Varietal denomination: 'Faith'.

BACKGROUND

The new and distinct cultivar of grape named 'Faith' is described herein. The new cultivar originated from a hand-pollinated cross of A-1962 (female parent) and Jupiter (U.S. Plant Pat. No. 13,309; male parent) made in 1990. The seedlings fruited in the summer of 1992 in a vineyard near Clarksville, Ark. and one was selected for its seedless, medium large, non-slipskin blue/black berries. The fruit grows in medium sized clusters, the vines have medium vigor and the plants are healthy.

SUMMARY OF THE INVENTION

The new and distinct cultivar of grapevine originated from a hand-pollinated cross of A-1962 (non-patented, non-released breeding genotype; female parent)×Jupiter (U.S. Plant Pat. No. 13,309; male parent) made in 1990 near Clarksville, Ark. The instant cultivar is a hybrid of *Vitis labrusca* L. and *Vitis vinifera* L. The seeds resulting from this controlled hybridization were germinated in a greenhouse during the winter of 1990-91. Resulting seedlings were planted in the spring of 1991 in a vineyard near Clarksville, Ark. The seedlings fruited in the summer of 1993 and one seedling, designated Arkansas Selection 2412, was selected for its seedless, blue, non-slipskin berries of mostly neutral but occasionally slight fruity flavor, medium sized clusters, medium vigor, and healthy plant.

During late 1993 and early 1994, the original plant selection was propagated asexually at the above-noted location, by rooting hardwood cuttings and a test planting of three vines was established. In all propagations hardwood cuttings were used and the instant cultivar rooted readily from hardwood cuttings. All propagules (resulting plants) of the instant cultivar have been observed to be true to type in that during all asexual multiplication, the vegetative and fruit characteristics of the original plant have been maintained. All vines planted from hardwood cutting propagation fruited in the second or third season of growth in the vineyard after planting.

Vines of the new cultivar have medium vigor, with a procumbent growth habit characteristic of *V. labrusca*. It has produced well as own-rooted plants in all testing and has not been evaluated on any rootstocks. Hardiness of the vines has been very good, with no winter injury to the vines to 5° F. in the most severe winters at the Arkansas test site.

The new cultivar is moderately resistant to powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopora viticola* Berl. & Tomi.), and anthrancnose (*Elsinoe ampelina* (d. By.) Sher), but susceptible to black rot (*Guignardia bidwellii* (Ell.) V. & R.). Fungal diseases can be controlled by the use of available fungicides.

The new cultivar ripens its fruit in the early season, from late July to early August. The fruit is blue in color at early maturity. It is evenly colored within the cluster. The fruit shape is oval. Fruit skins adhere to the flesh (has a non-slipskin texture). The berries are medium (ca. 4.5 g). The flavor is neutral with an occasional slight fruity flavor. Solids concentration of the juice at fruit maturity averages 19% with medium acidity. The fruit is of the stenospermocarpic type of seedlessness and can contain 1-2 small, soft vestigial seed traces that are not noticeable when eaten. Fruit clusters, borne usually one to two per shoot, are medium sized with an average weight of 150 to 250 g.

The new cultivar has been named the 'Faith' cultivar.

BRIEF DESCRIPTION OF THE PHOTOGRAPHS

The accompanying photographs show typical specimens of the new variety at 9 years of age in color as nearly true as it is reasonably possible to make in a color illustration of this character.

DETAILED DESCRIPTION OF THE NEW CULTIVAR

Figure 1:
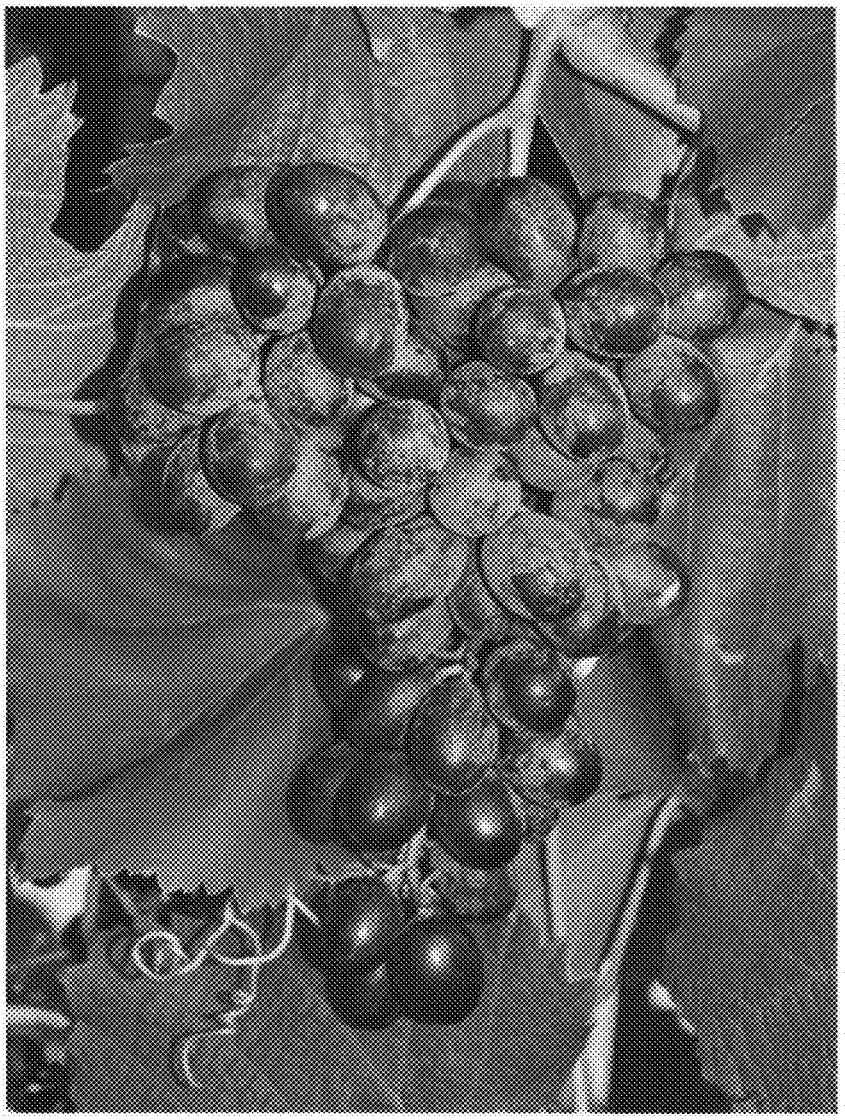
FIG. 1 is a photograph showing typical specimens of the fruit.
Figure 2:
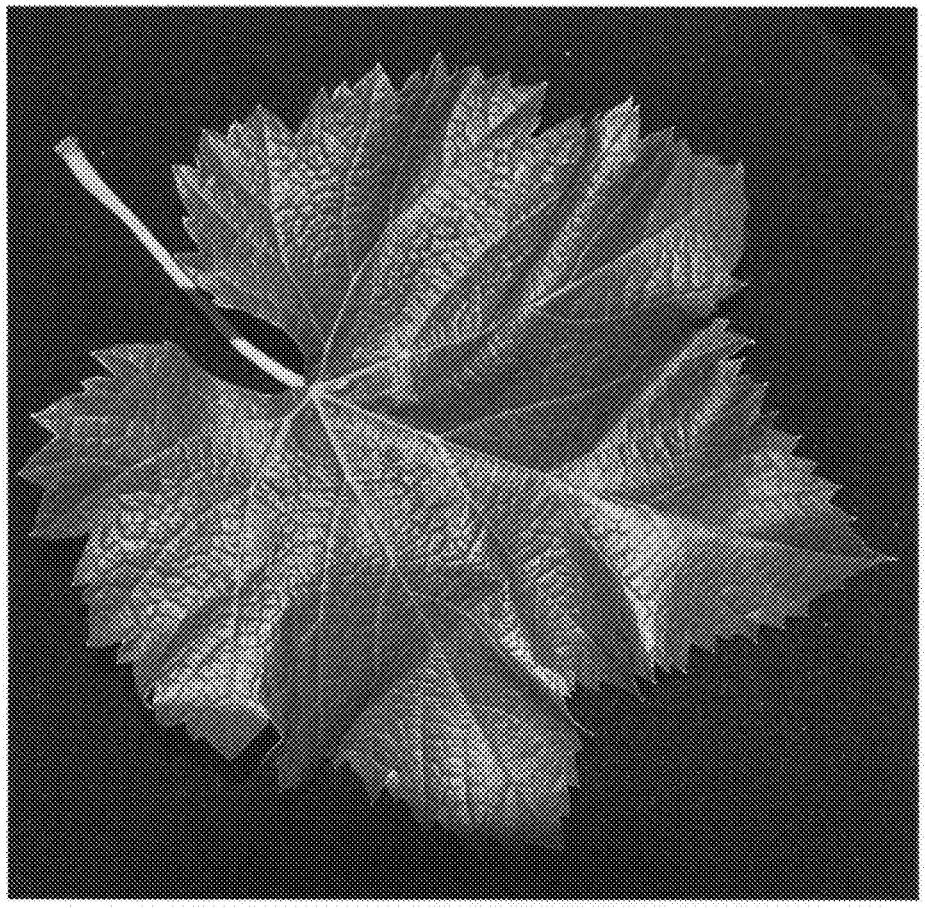
FIG. 2 is a photograph showing the leaf adaxial view.
Figure 3:
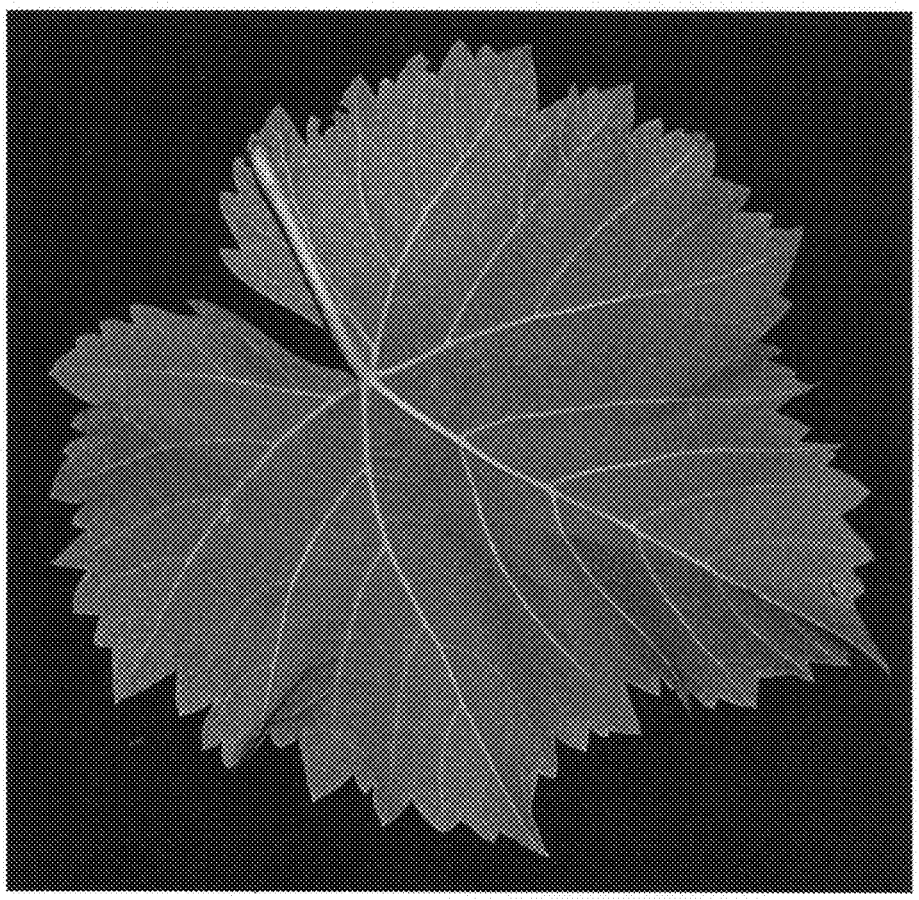
FIG. 3 is a photograph showing the leaf abaxial view.

'Faith' differs from its female parent A-1962 in that 'Faith' has firmer texture, has smaller berries, is more productive, and is seedless. 'Faith' differs from it male parent 'Jupiter' as this parent is reddish blue, has smaller clusters and has a distinct muscat flavor.

The following is a detailed description of the botanical and pomological characteristics of the subject grapevine. Color data are presented in Royal Horticultural Society Colour Chart designations, 1986 version, second edition.

Where dimensions, sizes, colors and other characteristics are given, it is to be understood that such characteristics are approximations of averages set forth as accurately as practicable.

The descriptions reported herein are from specimens grown near Clarksville, Ark. Vines used for measurement were irrigated using trickle (drip) irrigation. The data collection was from vines that were 15 years old.

Vine:

*Size.*—Medium.

*Growth.*—Moderately vigorous.

*Density of foliage.*—Medium.

*Productivity.*—Moderate.

*Rootstock.*—None; vines tested were own-rooted vines.

*Cold hardiness.*—Hardy to 5° C. (−15° C.); possibly more hardy as this was the coldest temperature experienced at the test site.

*Shoots* (*current-season canes*).—Color of shoots on the side exposed to direct sunlight — Greyed-Purple Group (184A). Color on the side shaded from the sun Yellow-Green Group (146C). Anthocyanin present on the shoot sides exposed to direct sunlight. Shoot attitude is procumbent.

*Canes* (*mature measured in winter*).—Color of mature cane: base mostly Greyed-Orange Group (165A); midpoint Greyed-Green Group (188D) overlaying Greyed-Orange Group (165A); terminal Greyed-Orange Group (165A); anthocyanin not observed on mature canes at base, midpoint, or terminal. Length average 2.8 m with range of 2.3-3.1 m. Diameter of mature cane: base 1.1 cm, midpoint 0.8 cm, terminal 0.5 cm. Internode length: base 8.1 cm, midpoint 12.4 cm, terminal 9.1 cm. Lenticels present on mature canes at heavy density and small (less than 0.5 mm in diameter). Canes mature to tips in the fall.

*Trunk.*—Shape — slender. Trunk straps — long, split. Surface texture — shaggy. Inner bark color — Greyed-orange group (177B). Outer bark color — Grey group, (201D).

Foliage:

*Leaves.*—Leaves simple and alternate; shape orbicular; number of lobes 1; petiole sinus shape half open; venation palmate-pinnate; margin serrated with shape of teeth convex and teeth medium in size. Color of mature leaves: base abaxial — Yellow-Green Group (147B); base adaxial — Green Group (137A); midpoint abaxial — Yellow-Green Group (147B); midpoint adaxial — Green Group (137A); terminal abaxial — Yellow-Green Group (147B); terminal adaxial — Green Group (137A). No anthocyanin on upper or lower surfaces of leaves or on leaf veins. Color of young leaves: base abaxial — Yellow-Green Group (146C); base adaxial — Yellow-Green Group (146B); midpoint abaxial — Yellow-Green Group (148C); midpoint adaxial — Yellow-Green Group (146C); terminal abaxial — Yellow-Green Group (148D); terminal adaxial — Yellow-Green Group (146D). No anthocyanins on upper or lower surfaces of leaves or on leaf veins.

*Petioles.*—Color on young leaves — Greyed-Purple Group (184A). Color of mature petioles — abaxial Yellow-Green Group (146D); adaxial Greyed-Purple Group (184B). Petiole anthocyanin present mostly on the sunlit side. Sinus of mature leaf is 4.4 cm deep and 1.2 cm at widest point. Mature leaves have sparse pubescence. Young leaves have sparse to medium pubescence that is prostrate.

*Tendrils.*—Found on almost every node, not opposite, and not spiraled. Length — 18.5 cm. Texture smooth and usually forked and curled on distal end. Color of mature tendril — Greyed-Orange Group 165A.

*Buds.*—Average number of buds on a current, single-season cane — 26. Dormant bud (compound bud or eye) width 4.2 mm; shape rounded triangular. Color Greyed-Orange Group (165A). Texture smooth with some trichomes (slightly fuzzy).

Disease resistance: Moderately resistant to powdery mildew, and downy mildew; susceptible to black rot. Other disease or pest susceptibilities not known.

Flowers:

*Sex.*—Hermaphrodite.

*Date of bloom.*—May 9 (first); May 14 (full). Flowers per cluster — 491.

*Stamens.*—Number: 5 and erect. Color: Green-White Group (157A).

*Pistil.*—Number: 1. Length: 3.6 mm. Color: Yellow-Green Group (144A).

*Pollen.*—Color: Yellow Group (10A), normal and fertile.

*Petal.*—Cap of 6 fused petals in tubular shape. Color Yellow-Green Group (147C).

*Sepal.*—None.

Fruit:

*Maturity.*—Early season; ripens late July to early August.

*Berry.*—Shape — Oval. Color — Greyed-Purple Group (187A). Size — Diameter at equator: 1.7 cm. Diameter at base: 1.4 cm. Diameter at apex: 1.4 cm. Length: 2.3 cm. Weight: 4.5 g; uniform in size. Texture — Non-slipskin. Skin thickness — Medium to thin. Seeds — 0 to 1 seed per berry and always soft. Brush length — 3.39 mm. Flavor — Neutral with occasional slight fruity flavor. Soluble solids — 19.0%.

*Juice.*—pH — 4.2. Titratable acidity — 2.78 g/L tartaric acid. Soluble solids — 19.0%.

*Cluster.*—Weight — 158.2 to 250.8 g; mean 204.5 g. Length — 19.9 cm. Width — 10.1 cm. Berries per cluster — 140-293, mean=195.2. Cluster per vine — 115. Clusters per shoot — one to two. Peduncle length — 1.93 cm. Pedicle: Length — 1.45 cm. Diameter — 0.47 cm. Color — Yellow-Green Group (146B). Use — Fresh consumption as a table grape is the primary use particularly for local markets. No processing evaluations done.

The cultivar: The most distinctive features of the cultivar are its seedless, blue, non-slipskin berries with neutral to occasional slight fruity flavor, medium sized clusters, medium vigor, and healthy plant.

We claim:

1. A new and distinct cultivar of grape plant named 'Faith' substantially as illustrated and described.

* * * * *